United States Patent
Hellerbrand et al.

(10) Patent No.: US 12,121,516 B2
(45) Date of Patent: Oct. 22, 2024

(54) PHARMACEUTICAL COMPOSITION COMPRISING SELEXIPAG

(71) Applicant: ACTELION PHARMACEUTICALS LTD, Allschwil (CH)

(72) Inventors: Klaus Hellerbrand, Martinsried (DE); Alexandra Schlicker-Spain, Allschwil (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 720 days.

(21) Appl. No.: 16/491,854

(22) PCT Filed: Mar. 7, 2018

(86) PCT No.: PCT/EP2018/055551
§ 371 (c)(1),
(2) Date: Sep. 6, 2019

(87) PCT Pub. No.: WO2018/162527
PCT Pub. Date: Sep. 13, 2018

(65) Prior Publication Data
US 2020/0129506 A1 Apr. 30, 2020

(30) Foreign Application Priority Data
Mar. 8, 2017 (WO) ................ PCT/EP2017/055406

(51) Int. Cl.
*A61K 31/4965* (2006.01)
*A61K 9/00* (2006.01)
*A61K 9/19* (2006.01)
*A61K 47/10* (2017.01)
*A61K 47/26* (2006.01)

(52) U.S. Cl.
CPC ........ *A61K 31/4965* (2013.01); *A61K 9/0019* (2013.01); *A61K 9/19* (2013.01); *A61K 47/10* (2013.01); *A61K 47/26* (2013.01)

(58) Field of Classification Search
CPC .... A61K 31/4965; A61K 47/10; A61K 47/26; A61K 9/0019; A61K 9/19; A61K 47/02; A61K 47/183; A61K 9/08; A61P 17/02; A61P 9/12
See application file for complete search history.

(56) References Cited

U.S. PATENT DOCUMENTS

| | | | |
|---|---|---|---|
| 8,791,122 B2 * | 7/2014 | Itou ........................... | A61P 9/00 |
| 2014/0303245 A1 | 10/2014 | Sprogøe et al. | |
| 2015/0272874 A1 | 10/2015 | Sawa et al. | |
| 2018/0325895 A1 | 11/2018 | Furuta et al. | |
| 2018/0333413 A1 | 11/2018 | Furuta et al. | |
| 2021/0030877 A1 | 2/2021 | Larson et al. | |

FOREIGN PATENT DOCUMENTS

| | | | | |
|---|---|---|---|---|
| CA | 2764475 A1 | 12/2010 | | |
| EP | 2 893 922 A1 | 7/2015 | | |
| EP | 3344607 | * 1/2016 | | |
| EP | 3192502 A1 | 7/2017 | | |
| KR | 10-2014-0082649 A | 7/2014 | | |
| KR | 10-2016-0055243 A | 5/2016 | | |
| WO | WO 02/088084 A1 | 11/2002 | | |
| WO | WO-03072082 A1 | * 9/2003 | ........... | A61K 31/395 |
| WO | WO 2009/107736 A1 | 9/2009 | | |
| WO | WO 2009/154246 A1 | 12/2009 | | |
| WO | WO 2009/157396 A1 | 12/2009 | | |
| WO | WO 2009/157397 A1 | 12/2009 | | |
| WO | WO 2009/157398 A1 | 12/2009 | | |
| WO | WO 2010/150865 A1 | 12/2010 | | |
| WO | WO 2011/024874 A1 | 3/2011 | | |
| WO | WO-2012143012 A1 | * 10/2012 | ........... | A61K 31/557 |
| WO | WO 2013/024051 A1 | 2/2013 | | |
| WO | WO 2014/069401 A1 | 5/2014 | | |
| WO | 2017/029594 A1 | 2/2017 | | |
| WO | WO 2017/098998 A1 | 6/2017 | | |

OTHER PUBLICATIONS

Actelion (Selexipag / ACT-293987, Pulmonary Arterial Hypertension, Jan. 2017, pp. 2-72).*
Uptravi (Highlights of Prescribing Information, Reference ID: 3864143, Dec. 2015, pp. 1-21).*
Sigma (Tween 20, ProductInformation, May 2003).*
Meyer (Impact of bulking agents on the stability of a lyophilized monoclonal antibody, European Journal of Pharmaceutical Sciences, 38 (2009), pp. 29-38).*
Gen (lyophilization: Growing with Biotechnology, Sep. 15, 2005, Lyophilization: Growing with Biotechnology (genengnews.com)).*
Mehood et al. "Excipients Use in Parenteral and Lyophilized Formulation Development," Open Science Journal of Pharmacy and Pharmacology 2015; 3(3): 19-27 (Year: 2015).*
Asaki et al., "Structure—Activity Studies on Diphenylpyrazine Derivatives: A Novel Class of Prostacyclin Receptor Agonists," *Bioorganic & Medicinal Chemistry*, 2007, vol. 15: 6692-6704.
Asaki et al., "Selexipag: An Oral and Selective IP Prostacyclin Receptor Agonist for the Treatment of Pulmonary Arterial Hypertension," *Journal of Medicinal Chemistry*, 2015, vol. 58: 7128-7137.

(Continued)

*Primary Examiner* — Jeffrey S Lundgren
*Assistant Examiner* — Michael J Schmitt
(74) *Attorney, Agent, or Firm* — BakerHostetler

(57) ABSTRACT

The invention relates to aqueous pharmaceutical compositions comprising the compound 2-{4-[N-(5,6-diphenylpyrazin-2-yl)-N-isopropylamino]butyloxy}-N-(methylsulfonyl) acetamide; glycine; polysorbate 20; and an aqueous phosphate buffer, wherein the relative amounts are as described in the description, wherein the pH of said pharmaceutical composition is between about 7 and 8; to lyophilized pharmaceutical compositions prepared from said aqueous compositions, and to reconstituted aqueous compositions thereof which are suitable for i.v. administration. The invention further relates to processes for the preparation of said compositions, and to their use for the treatment of diseases and disorders which are related to IP receptor.

17 Claims, No Drawings

(56) References Cited

OTHER PUBLICATIONS

Hurst et al., "Absolute oral bioavailability of selexipag, a novel oral prostacyclin IP receptor agonist, in healthy subjects," Poster presented at the American College of Clinical Pharmacology annual meeting, Sep. 25-27, 2016, Bethesda, MD, USA.
Ichikawa et al., "Pharmacokinetics of the selective prostacyclin receptor agonist selexipag in rats, dogs and monkeys," *Xenobiotica*, 2018, vol. 48(2): 186-196.
Kaufmann et al., "Absolute oral bioavailability of selexipag, a novel oral prostacyclin IP receptor agonist," *Eur J Clin Pharmacol*, 2017, vol. 73:151-156.
Kuwano et al., "2-{4-[(5,6-Diphenylpyrazin-2-yl)(isopropyl)amino]butoxy }-N-(methylsulfonyl)acetamide (NS-304), an Orally Available and Long-Acting Prostacyclin Receptor Agonist Prodrug," *The Journal of Pharmacology and Experimental Therapeutics*, 2007, vol. 322(3): 1181-1188.
Kuwano et al., "A Long-Acting and Highly Selective Prostacyclin Receptor Agonist Prodrug, 2-{4-[(5,6-Diphenylpyrazin-2-yl)(isopropyl)amino]butoxy}-N-(methylsulfonyl)acetamide(NS-304), Ameliorates Rat Pulmonary Hypertension with Unique Relaxant Responses of Its Active Form, { 4-[(5,6-Diphenylpyrazin-2-yl)(isopropyl)amino]butoxy}acetic Acid (MRE-269), on Rat Pulmonary Artery," *The Journal of Pharmacology and Experimental Therapeutics*, 2008, vol. 326(3):691-699.
Nakamura et al., "Synthesis and Evaluation of N-acylsulfonamide and N-acylsulfonylurea Prodrugs of a Prostacyclin Receptor Agonist," *Bioorganic & Medicinal Chemistry*, 2007, vol. 15: 7720-7725.
"Safety Study of the Switch From Oral Selexipag to Intravenous Selexipag in Subjects With Stable Pulmonary Arterial Hypertension," ClinicalTrials.gov, Identifier: NCT03187678, 2017, 8 pages.
Remington, "Pharmaceutical Manufacturing," *The Science and Practice of Pharmacy*, 2005, 21$^{st}$ Edition, Part 5.
Rowe et al., Handbook of Pharmaceutical Excipients, 2006, 6$^{th}$ Edition, 917 pages.
Sardana et al., "Pharmacokinetic Drug Evaluation of Selexipag for the Treatment of Pulmonary Arterial Hypertension," *Expert Opinion on Drug Metabolism & Toxicology*, 2016, vol. 12(12): 1513-1520.
Sitbon et al., "Selexipag for the Treatment of Pulmonary Arterial Hypertension," *The New England Journal of Medicine*, 2015, vol. 373(26): 2522-2533.
Baheti, A., et al., "Excipients used in lyophilization of small molecules," Journal of Excipients and Food Chemicals, vol. 1, No. 1, Jan. 2010, pp. 41-54.
Gibson (Ed.), "Pharmaceutical Preformulation and Formulation: A Practical Guide from Candidate Drug Selection to Commercial Dosage Form (2nd ed.)", 2009, CRC Press, cover pages & Chapter 9, pp. 325-347.
J. Swarbrick (Ed.), Encyclopedia of Pharmaceutical Technology (3rd ed.), 2007, CRC Press, cover pages & pp. 1001-1011; 1622-1645; and 1807-1833.
Mehmood, Y., et al., "Excipients Use in Parenteral and Lyophilized Formulation Development," Open Science Journal of Pharmacy and Pharmacology, vol. 3, No. 3, Jul. 20, 2015, pp. 19-27.
Tang, Xiaolin et al., "Design of Freeze-Drying Processes for Pharmaceuticals: Practical Advice" Pharmaceutical Research, Feb. 2004, 21(2) ,191-200.
Uptravi: EPAR public assessment report, Apr. 1, 2016, pp. 1-117.
Wang, W., "Tolerability of hypertonic injectables," International Journal of Pharmaceutics, Vo. 490, No. 1-2, May 2015, pp. 308-315.
Warne, N.W., "Development of high concentration protein biopharmaceuticals: the use of platform approaches in formulation development," European Journal of Pharmaceutics and Biopharmaceutics, vol. 78, No. 2, 2011, pp. 208-212.

* cited by examiner

PHARMACEUTICAL COMPOSITION COMPRISING SELEXIPAG

CROSS-REFERENCE TO RELATED APPLICATIONS

This application is a National Stage Entry under 35 U.S.C. § 371 of International Application No. PCT/EP2018/055551, filed Mar. 7, 2018, which claims the benefit of PCT Application No. PCT/EP2017/055406, filed Mar. 8, 2017, the contents of each of which are incorporated by reference in their entireties.

The present invention relates to pharmaceutical compositions comprising 2-{4-[N-(5,6-diphenylpyrazin-2-yl)-N-isopropylamino]butyloxy}-N-(methylsulfonyl)acetamide (selexipag, NS-304, ACT-293987; hereinafter COMPOUND) which are suitable for intra venous (i.v.) administration.

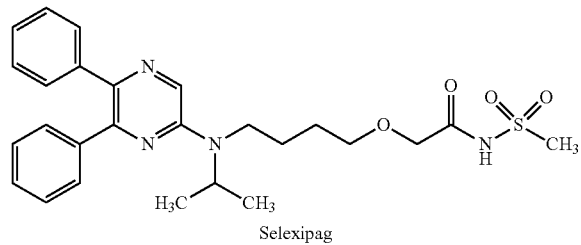 [SMILES: CC(C)N(CCCCOCC(=O)NS(C)(=O)=O)c1cnc(-c2ccccc2)c(-c2ccccc2)n1]

Selexipag

The preparation and the medicinal use of selexipag and its active metabolite 2-(4-((5,6-diphenylpyrazin-2-yl)(isopropyl)amino)butoxy)acetic acid (MRE-269, ACT-333679) is described in WO2002/088084; WO2009/157396; WO2009/107736; WO2009/154246; WO2009/157397; WO2009/157398; WO2010/150865; WO2011/024874; Nakamura et al., Bioorg Med Chem (2007), 15, 7720-7725; Kuwano et al., J Pharmacol Exp Ther (2007), 322(3), 1181-1188; Kuwano et al., J Pharmacol Exp Ther (2008), 326(3), 691-699; O. Sitbon et al., N Engl J Med (2015), 373, 2522-33; Asaki et al., Bioorg Med Chem (2007), 15, 6692-6704; Asaki et al., J. Med. Chem. (2015), 58, 7128-7137. Certain formulations are disclosed in WO2013/024051, and WO2014/069401.

Specifically, selexipag or its active metabolite may be useful as preventive or therapeutic agent for ulcer, digital ulcer, diabetic gangrene, diabetic foot ulcer, pressure ulcer (bedsore), hypertension, pulmonary hypertension, pulmonary arterial hypertension, Fontan disease and pulmonary hypertension associated with Fontan disease, sarcoidosis and pulmonary hypertension associated with sarcoidosis, peripheral circulatory disturbance (e.g., chronic arterial occlusion, intermittent claudication, peripheral embolism, vibration syndrome, Raynaud's disease), connective tissue disease (e.g., systemic lupus erythematosus, scleroderma, mixed connective tissue disease, vasculitic syndrome), reocclusion/restenosis after percutaneous transluminal coronary angioplasty (PTCA), arteriosclerosis, thrombosis (e.g., acute-phase cerebral thrombosis, pulmonary embolism), transient ischemic attack (TIA), diabetic neuropathy, ischemic disorder (e.g., cerebral infarction, myocardial infarction), angina (e.g., stable angina, unstable angina), chronic kidney diseases including glomerulonephritis and diabetic nephropathy at any stage, allergy, bronchial asthma, restenosis after coronary intervention such as atherectomy and stent implantation, thrombocytopenia by dialysis, the diseases in which fibrosis of organs or tissues is involved [e.g., renal diseases such as tubulointerstitial nephritis), respiratory diseases (e.g. (usual) interstitial pneumonia/(idiopathic) pulmonary fibrosis, chronic obstructive pulmonary disease), digestive diseases (e.g., hepatocirrhosis, viral hepatitis, chronic pancreatitis and scirrhous stomachic cancer), cardiovascular diseases (e.g., myocardial fibrosis), bone and articular diseases (e.g., bone marrow fibrosis and rheumatoid arthritis), skin diseases (e.g., cicatrix after operation, scalded cicatrix, keloid, and hypertrophic cicatrix), obstetric diseases (e.g., hysteromyoma), urinary diseases (e.g., prostatic hypertrophy), other diseases (e.g., alzheimer's disease, sclerosing peritonitis, type I diabetes and organ adhesion after operation)], erectile dysfunction (e.g., diabetic erectile dysfunction, psychogenic erectile dysfunction, psychotic erectile dysfunction, erectile dysfunction associated with chronic renal failure, erectile dysfunction after intrapelvic operation for removing prostata, and vascular erectile dysfunction associated with aging and arteriosclerosis), inflammatory bowel disease (e.g., ulcerative colitis, Crohn's disease, intestinal tuberculosis, ischemic colitis and intestinal ulcer associated with Behcet disease), gastritis, gastric ulcer, ischemic ophthalmopathy (e.g., retinal artery occlusion, retinal vein occlusion, ischemic optic neuropathy), sudden hearing loss, avascular necrosis of bone, intestinal damage caused by administration of a non-steroidal anti-inflammatory agent and symptoms associated with lumbar spinal canal stenosis.

Selexipag was shown to be beneficial in the treatment of pulmonary arterial hypertension. In a phase III clinical trial, among patients with pulmonary arterial hypertension, the risk of the primary composite end point of death or a complication related to pulmonary arterial hypertension was significantly lower among patients who received selexipag than among those who received placebo. Selexipag received market approval e.g. in the US and is indicated for the treatment of pulmonary arterial hypertension (PAH, WHO Group I) to delay disease progression and reduce the risk of hospitalization for PAH.

So far, standard film-coated tablet formulations of selexipag intended for twice daily oral administration have been used, wherein excipients comprise D-mannitol, corn starch, low substituted hydroxypropylcellulose, hydroxypropylcellulose, and magnesium stearate; and the tablets are film coated with a coating material containing hypromellose, propylene glycol, titanium dioxide, carnauba wax along with mixtures of iron oxides.

Selexipag is thought to function as a prodrug (while retaining some agonistic activity on the IP receptor on its own) which can exert long-lasting selective IP receptor agonist activity of the active metabolite 2-(4-((5,6-diphenylpyrazin-2-yl)(isopropyl)amino)butoxy) acetic acid in mammals, especially humans. The in vivo metabolism of selexipag effectively may act as a kind of 'slow-release mechanism' that potentially both prolongs activity and reduces typical adverse effects associated with high concentrations of PGI2 agonists (Kuwano et al., J Pharmacol Exp Ther (2007), 322(3), 1181-1188).

Adverse effects associated with PGI2 agonists are also addressed by a particular up-titration schedule. The recommended starting dose of oral selexipag is 200 micrograms given twice daily. The dose is then increased in increments of 200 micrograms twice daily, usually at weekly intervals, to the highest tolerated dose up to 1600 micrograms twice daily. If a patient reaches a dose that cannot be tolerated, the dose should be reduced to the previous tolerated dose.

In certain instances the use of an oral formulation of selexipag may be inappropriate or impossible (e.g. in urgent care, or in case a patient is for some reasons unable to swallow a tablet). Furthermore, treatment of certain diseases may only require short term treatment, or a treatment comprising alternating periods of treatment/non-treatment, in which case the above-mentioned up-titration schedule could be inappropriate. Such diseases may comprise for example ulcer, digital ulcer, diabetic gangrene, diabetic foot ulcer, pressure ulcer (bedsore), peripheral circulatory disturbances, etc. Therefore, there is a need to develop a stable and reproducible i.v. formulation for selexipag. In a Phase1 study "Absolute oral bioavailability of selexipag, a novel oral prostacyclin IP receptor agonist, in healthy subjects", selexipag was generally well tolerated when administered orally or by i.v. infusion (N. Hurst, P. Kaufmann, M. Richard, B. Astruc, J. Dingemanse, Poster presented at the American College of Clinical Pharmacology annual meeting, 25-27 Sep. 2016, Bethesda, USA). Moreover, a "Safety Study of the Switch from Oral Selexipag to Intravenous Selexipag in Subjects With Stable Pulmonary Arterial Hypertension" has been posted on 15 Jun. 2017 (https://clinicaltrials.gov/ct2/show/NCT03187678).

Particular difficulties in the development of such an i.v. formulation comprising selexipag arise from the fact that the required dosage of selexipag is likely to be in the microgram to single digit milligram range per day, requiring rigid quantitative control of the injected dose. For example, adsorption of active ingredient on syringes or tubing may have an impact on the suitability of a selexipag i.v. formulation. Furthermore, by the nature of selexipag being a hydrolysable prodrug, premature hydrolysis to the active metabolite should be prevented in such i.v. formulation. Stability including chemical stability may, therefore, be another important criterion, for the selection of a pharmaceutical composition suitable for i.v. administration.

It has now been found that only certain compositions comprising selexipag, a bulking agent, a detergent, and a buffer lead to chemically and physically stable aqueous formulations that can reproducibly be lyophilized to a stable cake and reconstituted to a controlled composition which is suitable for i.v. administration. Adsorption of active ingredient to tubings and syringes could be avoided.

1) A first embodiment relates to an aqueous pharmaceutical composition comprising:
  about 0.1 g/kg to 1 g/kg, especially about 0.5 g/kg (with respect to the total weight of said aqueous pharmaceutical composition) of the compound: 2-{4-[N-(5,6-diphenylpyrazin-2-yl)-N-isopropylamino]butyloxy}-N-(methylsulfonyl)acetamide:

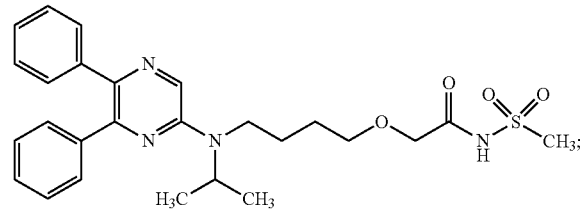 [SMILES: CC(C)N(CCCCOCC(=O)NS(C)(=O)=O)c1cnc(-c2ccccc2)c(-c2ccccc2)n1]

about 2.5 ww % to 10 ww % of a bulking agent which is glycine (notably about 3 ww % to 6 ww % of glycine; especially about 5 ww % of glycine) (i.e. about 25-100 g/kg; notably about 30-60 g/kg especially about 50 g/kg of glycine);

about 0.05 ww % to 0.4 ww % of a detergent which is polysorbate 20 (notably between about 0.1 ww % and 0.3 ww % of polysorbate 20; especially about 0.1, 0.2, or 0.3 ww % of polysorbate 20) (wherein preferably about 5-40 g/kg; notably between about 10 and 30 g/kg; especially about 10, 20, or 30 g/kg of an about 10 ww % aqueous solution of polysorbate 20 is used); and
  an aqueous phosphate buffer (especially an aqueous sodium phosphate buffer (i.e. an aqueous buffer composed of $H_3PO_4$ and NaOH)), wherein the total amount of said phosphate buffer is about 5 mmol/kg to 20 mmol/kg (with respect to the total weight of said aqueous pharmaceutical composition), in particular about 10 mmol/kg;
wherein the pH of said aqueous pharmaceutical composition is between about 7 and 8 (notably the pH is 7.5±0.3; especially 7.5±0.2).

The present compositions according to embodiment 1) are liquid isotropic mixtures, which contain COMPOUND in free base form. COMPOUND may be used for the preparation of the present compositions in amorphous, or in one or more crystalline forms, or in mixtures of amorphous and crystalline form(s). Crystalline forms may be anhydrous, or solvate or hydrate forms. Such morphological forms are encompassed in the scope of COMPOUND. Preferably COMPOUND is used in crystalline form. The present compositions encompass COMPOUND in essentially pure form. The amount of COMPOUND may be adjusted taking into account the actual chemical purity, or the presence of a solvate, or hydrate, of COMPOUND.

The term "bulking agent" refers to a substance or component that is chemically compatible with the active pharmaceutical ingredient and with further excipients of a composition, and that adds mass to a lyophilized composition. A bulking agent suitable for pharmaceutical compositions according to embodiment 1) of the present invention is glycine. Bulking agents typically used in pharmaceutical compositions are for example mannitol, trehalose, L-proline, and polyvinylpyrrolidone.

The excipient polysorbate 20 or polyoxyethylene (20) sorbitan monolaurate as used within the scope of the present invention refers to commercially available polysorbate 20 (CAS No 9005-64-5, E 432), preferably Tween® 20/Tween® 20 EMPROVE® from Croda Americas/Merck Chemicals. Alternative commercial forms of polysorbate 20 are for example Armotan® PML 20; Capmul® POE-L; Crillet™ 1; Eumulgin® SML 20; Glycosperse® L-20; Liposorb® L-20; Montanox™ 20; Nonion® LT-221; Ritabate 20; Sorbax PML-20; T-Maz® 20; Protasorb™ L-20; Tego® SML 20; Alkest® TW 20; Wilsurf® TF-20.

Polysorbate 20 may be defined as (non-ionic) detergent/emulsifyer/surfactant. Detergents, especially commercially available detergent products, are usually not pure compounds but may be rather complex mixtures of compounds containing one primary major detergent component. Polysorbate 20 for example is a polysorbate-type nonionic detergent formed by the ethoxylation of sorbitan before the addition of lauric acid. The ethoxylation process leaves the molecule with 20 repeat units of polyethylene glycol; in practice these are distributed across 4 different chains leading to a commercial product containing a range of chemical species. Polysorbate 20 may contain variable amounts of said primary major detergent component, and residual amounts of further components such as for example residual polyethyleneglycols (which may stem from the chemical production process). The above-mentioned variation in the chemical species and the residual further components possibly comprised in the commercial product are encompassed in the scope of term "polysorbate 20" as used herein.

The total ww % of the pharmaceutical compositions as defined in embodiment 1), and embodiments 2) to 6) below is 100.

For avoidance of any doubt, it is well understood that pharmaceutical compositions as defined in embodiment 1) and 2) to 6) below may additionally comprise further conventional ingredients and/or additives, which may be used alone or in combination (quantum satis, i.e. wherein the maximum amounts of said further conventional ingredients and/or additives may need to be reduced to make up the total ww % of 100). It is understood that the pharmaceutical compositions as defined in embodiment 1) and 2) to 6) below will not comprise a further bulking agent or a further detergent.

Reference is made to the extensive literature on the subject for these and other pharmaceutically acceptable excipients and procedures mentioned herein, see for example R. C. Rowe, P. J. Seskey, S. C. Owen, Handbook of Pharmaceutical Excipients, 5th edition, Pharmaceutical Press 2006; Remington, *The Science and Practice of Pharmacy*, 21st Edition (2005), Part 5, "Pharmaceutical Manufacturing" [published by Lippincott Williams & Wilkins].

Examples of such conventional ingredients or additives are tonicity modifiers such as salts (e.g. NaCl, KCl, $MgCl_2$, $CaCl_2$). Further conventional ingredients or additives are for example antimicrobial preservatives such as used e.g. in bacteriostatic water for injection. An example is benzyl alcohol.

The absolute amounts of each pharmaceutically acceptable excipient and the amounts relative to other pharmaceutically acceptable excipients are dependent on the desired properties of the pharmaceutical composition and can be chosen by routine experimentation.

The total weight percent of the pharmaceutical composition is 100.

The term "pharmaceutical composition" is interchangeable with the terms "formulation", or "composition".

Unless used regarding temperatures, the term "about" placed before a numerical value "X" refers in the current application to an interval extending from X minus 10% of X to X plus 10% of X, and preferably to an interval extending from X minus 5% of X to X plus 5% of X (wherein it is well understood that percent values below 0%, respectively higher than 100%, are not applicable). In case the term about is placed before a range, the respective interval is to be applied to both values of the range. In case the term about is placed before a list of particular values, the respective interval is to be applied to all values of the list. For example, about 10, 20, or 30 g/kg of an about 10 ww % aqueous solution of polysorbate 20 refer to 10±1, 20±2, or 30±3 g/kg of a 10±1 ww % aqueous solution of polysorbate 20; preferably to 10±0.5, 20±1, or 30±1.5 g/kg of a 10±0.5 ww % aqueous solution of polysorbate 20. In the particular case of temperatures, the term "about" placed before a temperature "Y" refers in the current application to an interval extending from the temperature Y minus 10° C. to Y plus 10° C.; and preferably, in case the temperature is at least 30° C. to an interval extending from Y minus 5° C. to Y plus 5° C.; or, in case the temperature is below 30° C., to an interval extending from Y minus 2° C. to Y plus 2° C.

Whenever the word "between" or "to" is used to describe a numerical range, it is to be understood that the end points of the indicated range are explicitly disclosed and included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The expression "ww %" (or % (w/w)) refers to a percentage by weight compared to the total weight of the composition considered. If not explicitly stated otherwise, the considered total weight is the total weight of the pharmaceutical composition. In case a certain value is given as % value, in absence of further specification such value refers to ww %. The expression (wt/wt) relating to a ratio refers to a ratio by weight of the respective components.

The term "consisting essentially of" is understood in the context of the present invention to mean especially that the respective composition consists in an amount of at least 90, notably of at least 95, especially of at least 99, and preferably in an amount of 100 percent by weight (i.e. in the meaning of "consisting of") of the respective composition in the amounts as explicitly stated in the respective embodiment. The term "comprising" is preferably to be understood in the meaning of the term "consisting essentially of".

The term "essentially", for example when used in a term such as "essentially pure" is understood in the context of the present invention to mean especially that the respective composition/compound etc. consists in an amount of at least 90, especially of at least 95, and notably of at least 99 percent by weight of the respective pure composition/compound etc.

Further embodiments of the invention are presented hereinafter:

2) In another embodiment, the invention relates to a pharmaceutical composition according to embodiment 1), comprising:
  about 0.1 g/kg to 1 g/kg, especially about 0.5 g/kg of the compound: 2-{4-[N-(5,6-diphenylpyrazin-2-yl)-N-isopropylamino]butyloxy}-N-(methylsulfonyl)acetamide;
  about 3 ww % to 6 ww % of glycine; especially 5±0.5 ww % of glycine (i.e. 50±5 g/kg of glycine);
  about 0.1 ww % to 0.3 ww % (especially about 0.1 ww %, 0.2 ww %, or 0.3 ww %) of polysorbate 20 (wherein preferably about 10 g/kg, 20 g/kg, or 30 g/kg of an about ww % aqueous solution of polysorbate 20 is used); and
  aqueous sodium phosphate buffer (composed of $H_3PO_4$ and NaOH), wherein the concentration of said sodium phosphate buffer is about 5 mmol/kg to 20 mmol/kg, in particular about 10 mmol/kg;
wherein the pH of said pharmaceutical composition is 7.5±0.2.

3) In another embodiment, the invention relates to a pharmaceutical composition according to embodiment 1), comprising:
  about 0.1 g/kg to 1 g/kg, especially about 0.5 g/kg of the compound: 2-{4-[N-(5,6-diphenylpyrazin-2-yl)-N-isopropylamino]butyloxy}-N-(methylsulfonyl)acetamide;
  5±0.5 ww % of glycine (i.e. 50±5 g/kg of glycine);
  about 0.3 ww % of polysorbate 20 (wherein preferably about 30 g/kg of an about 10 ww % aqueous solution of polysorbate 20 is used); and
  aqueous sodium phosphate buffer (i.e. an aqueous buffer composed of $H_3PO_4$ and NaOH), wherein the concentration of said sodium phosphate buffer is about 5 mmol/kg to 20 mmol/kg, in particular about 10 mmol/kg;
wherein the pH of said pharmaceutical composition is 7.5±0.2.

4) In another embodiment, the invention relates to a pharmaceutical composition according to embodiment 1), comprising:
  about 0.1 g/kg to 1 g/kg, especially about 0.5 g/kg of the compound: 2-{4-[N-(5,6-diphenylpyrazin-2-yl)-N-isopropylamino]butyloxy}-N-(methylsulfonyl)acetamide;
  5±0.5 ww % of glycine (i.e. 50±5 g/kg of glycine);
  about 0.2 ww % of polysorbate 20 (wherein preferably about 20 g/kg of an about 10 ww % aqueous solution of polysorbate 20 is used); and
  aqueous sodium phosphate buffer (i.e. an aqueous buffer composed of $H_3PO_4$ and NaOH), wherein the concentration of said sodium phosphate buffer is about 5 mmol/kg to 20 mmol/kg, in particular about 10 mmol/kg;
wherein the pH of said pharmaceutical composition is 7.5±0.2.

5) In another embodiment, the invention relates to a pharmaceutical composition according to embodiment 1), comprising:
  about 0.1 g/kg to 1 g/kg, especially about 0.5 g/kg of the compound: 2-{4-[N-(5,6-diphenylpyrazin-2-yl)-N-isopropylamino]butyloxy}-N-(methylsulfonyl)acetamide;
  5±0.5 ww % of glycine (i.e. 50±5 g/kg of glycine);
  about 0.1 ww % of polysorbate 20 (wherein preferably about 10 g/kg of an about 10 ww % aqueous solution of polysorbate 20 is used); and
  aqueous sodium phosphate buffer (i.e. an aqueous buffer composed of $H_3PO_4$ and NaOH), wherein the concentration of said sodium phosphate buffer is about 5 mmol/kg to 20 mmol/kg, in particular about 10 mmol/kg;
wherein the pH of said pharmaceutical composition is 7.5±0.2.

6) In another embodiment, the invention relates to a pharmaceutical composition according to any one of embodiments 1) to 5), wherein the compound 2-{4-[N-(5,6-diphenylpyrazin-2-yl)-N-isopropylamino]butyloxy}-N-(methylsulfonyl)acetamide in crystalline form, especially in essentially pure crystalline form (preferably in essentially pure crystalline form I or essentially pure crystalline form II as disclosed in WO2010/150865), is used for the preparation of said composition.

The pharmaceutical composition according to the present invention will, prior to freeze drying, preferably be filled into containers (unit dose or multi-dose containers such as vials) suitable for storage of the lyophilized cake, and suitable for the later reconstitution of the pharmaceutical composition. Such containers may be filled under an inert gas atmosphere (such as notably a nitrogen atmosphere). Such inert gas atmosphere may reduce oxidative degradation of the active ingredient. A further embodiment thus relates to a container such as for example a vial, an ampoule, a syringe, a coupled chamber device, a pen device, or an autoinjector device, especially a vial, filled with a pharmaceutical composition according to any one of embodiments 1) to 6).

7) A further embodiment relates to a method for the preparation of a lyophilized pharmaceutical composition (i.e. a lyophilized cake); said method pharmaceutical comprising the steps of:
  a) preparing an aqueous pharmaceutical composition according to any one of embodiments 1) to 6); and
  b) freeze-drying said aqueous pharmaceutical composition to form a cake using a method comprising the steps of:
    (i) freezing the aqueous pharmaceutical composition at a first temperature for a period sufficient to transform the liquid formulation into solid state (especially for a period of at least about 1 hour), wherein said first temperature is in the range of about −55° C. to −25° C. (especially about −45° C.);
    (ii) annealing the frozen composition at a second temperature (notably for a period of at least about 1 hour, especially at least about 2 hours); wherein said second temperature is in the range of about −20° C. to −1° C. (notably about −10° C. to −2° C.; especially about −3° C.);
    (iii) subjecting the frozen composition to a vacuum (notably a vacuum of about 0.1 to 1.5 mbar, especially about 0.2 to 1.2 mbar, in particular 0.5±0.1 mbar) at a third temperature wherein said third temperature is in the range of about −55° C. to −25° C. (especially about −45° C.); and
    (iv) drying the composition in said vacuum at a fourth temperature (notably for a period of at least about 2 hours, especially of at least about 5 hours, in particular between about 5 to 15 hours, about 5 to 19 hours, preferably between about 5 to 22 hours or between 5 to 15 hours) wherein said fourth temperature is in the range of about 20° C. to 40° C.; notably in the range of about 25° C. to 35° C.; especially about 35° C.
    (v) optionally, the composition may be hold at a closing temperature of about 20° C. to 35° C., preferably 20° C.

The term "cake" refers to a dry solid material that results when a liquid formulation has been lyophilized or freeze dried.

8) A further embodiment relates to a lyophilized pharmaceutical composition prepared by lyophilizing an aqueous pharmaceutical composition according to any one of embodiments 1) to 6); especially by using the method of embodiment 7).

9) In another embodiment, the invention relates to a lyophilized pharmaceutical composition according to embodiment 8); wherein said lyophilized pharmaceutical composition is in a container; notably in a vial or in a syringe; especially in a vial.

10) In another embodiment, the invention relates to a lyophilized pharmaceutical composition according to embodiments 8) or 9); wherein said lyophilized pharmaceutical composition has a residual water content of less than about 2 ww % (e.g. as determined using a Karl Fischer analysis); notably less than about 1.5 ww %.

11) In another embodiment, the invention relates to a lyophilized pharmaceutical composition according to any one of embodiments 7) to 10); wherein said lyophilized pharmaceutical composition is chemically stable at room temperature and a relative humidity of about 75% or below (especially at about 25° C. and about 60% rH) for at least 6 month.

12) In another embodiment, the invention relates to a lyophilized pharmaceutical composition according to any one of embodiments 7) to 10); wherein said lyophilized pharmaceutical composition is chemically stable at about 2-8° C. and a relative humidity of about 75% or below (especially about 60% rH) for at least 12 month.

13) In another embodiment, the invention relates to a lyophilized pharmaceutical composition according to any one of embodiments 7) to 10); wherein the cake of said lyophilized pharmaceutical composition is physically stable at room temperature and a relative humidity of about 75% or below (especially at about 25° C. and about 60% rH) for at least 6 month.

14) A further embodiment relates to a method for the preparation of a reconstituted pharmaceutical composition; said method comprising the step of reconstituting the lyophilized pharmaceutical composition according to any one of embodiments 8) to 13) by adding at least one diluent to said lyophilized composition.

Suitable diluents to reconstitute said pharmaceutical composition include any diluent that is a safe, stable and pharmaceutically acceptable carrier. Preferred is water for injection (WFI) such as especially sterile water for injection (SWFI) or bacteriostatic water for injection (BWFI), optionally containing a tonicity modifier, or mixtures of several tonicity modifiers. Preferred diluents are WFI and especially aqueous (preferably physiological) saline.

15) In another embodiment, the invention relates to a method according to embodiment 20); wherein said diluent is water for injection or saline (notably saline, especially physiological saline/aqueous saline which has a concentration of about 0.9 ww %).

16) In another embodiment, the invention relates to a method according to embodiments 14) or 15); wherein said reconstituted pharmaceutical composition is further diluted with a second diluent (especially diluted to a total volume of about 50 mL) (wherein it is understood that said second diluent may be the same or different from the first diluent).

17) In another embodiment, the invention relates to a method according to embodiment 16); wherein said second diluent is saline, especially physiological saline/aqueous saline which has a concentration of about 0.9 ww %.

18) A further embodiment relates to a reconstituted pharmaceutical composition prepared from a lyophilized pharmaceutical composition according to any one of embodiments 8) to 13); especially prepared according to the method of embodiments 14) or 15); wherein especially said reconstituted pharmaceutical composition is reconstituted using, as diluent, water for injection (especially sterile water for injection) or saline (especially physiological saline/aqueous saline which has a concentration of about 0.9 ww %).

19) In another embodiment, the invention relates to a reconstituted pharmaceutical composition according to embodiment 18); wherein said reconstituted pharmaceutical composition is in a container; notably a vial, an ampoule, or a syringe; especially in a vial.

20) In another embodiment, the invention relates to a reconstituted pharmaceutical composition according to embodiments 18) or 19); wherein said reconstituted pharmaceutical composition is reconstituted in a reconstitution time of less than about 2 minutes, notably in about 1 minute or less, especially in about 30 seconds or less.

21) In another embodiment, the invention relates to a reconstituted pharmaceutical composition according to any one of embodiments 18) to 20); wherein said reconstituted pharmaceutical composition is reconstituted using, as diluent, water for injection (especially sterile water for injection) or saline (especially physiological saline/aqueous saline which has a concentration of about 0.9 ww %); wherein the total volume of said reconstituted pharmaceutical composition is notably between about 2 and 10 mL, especially between about 3 and 4.5 mL, or preferably between about 8 and 8.5 mL.

22) In another embodiment, the invention relates to a reconstituted pharmaceutical composition according to any one of embodiments 18) to 21); wherein said reconstituted pharmaceutical composition has an osmolality of below about 1500 mOsmol/kg, especially below about 1000 mOsmol/kg, in particular an osmolality of below about 950 mOsmol/kg; wherein the total volume is especially between about 8 mL and 8.5 mL.

23) In another embodiment, the invention relates to a reconstituted pharmaceutical composition according to any one of embodiments 18) to 22); wherein said reconstituted pharmaceutical composition contains about 0.1 to 0.5 mg/mL, especially about 0.225 mg/mL of the compound: 2-{4-[N-(5,6-diphenylpyrazin-2-yl)-N-isopropylamino]butyloxy}-N-(methylsulfonyl)acetamide.

24) A further embodiment relates to a reconstituted pharmaceutical composition for i.v. administration according to any one of embodiments 18) to 23); wherein said reconstituted pharmaceutical composition, or a part of said reconstituted pharmaceutical composition, is further diluted (especially further diluted to a total volume of about 50 mL); especially according to the method of embodiments 16) or 17); wherein said reconstituted and further diluted pharmaceutical composition contains an amount of about 4.5 µg/mL, 9 µg/mL, 13.5 µg/mL, 18 µg/mL, 22.5 µg/mL, 27 µg/mL, 31.5 µg/mL, or 36 µg/mL of the compound 2-{4-[N-(5,6-diphenylpyrazin-2-yl)-N-isopropylamino]butyloxy}-N-(methylsulfonyl)acetamide; wherein the tolerance of said amounts is notably 10%, especially 5%.

25) In another embodiment, the invention relates to a reconstituted and further diluted pharmaceutical composition according to embodiment 24); wherein said reconstituted and further diluted pharmaceutical composition is further diluted using saline (especially hypotonic or physiological saline, in particular physiological saline/aqueous saline which has a concentration of about 0.9 ww %); wherein especially the total volume of said reconstituted and further diluted pharmaceutical composition is 50 mL.

26) In another embodiment, the invention relates to a reconstituted and further diluted pharmaceutical composition according to embodiments 24) or 25); wherein said reconstituted and further diluted pharmaceutical composition has an osmolality of below about 1000 mOsmol/kg (especially below about 500 mOsmol/kg, in particular it is about isotonic).

Osmolality is a measurement of a fluids concentration which is represented by the number of solutes per kg of fluid. The normal osmolality of extracellular fluid in the human body is about 275-295 mOsmol/kg. Hypertonic solutions have an osmolality higher than the extracellular fluid (above about 350 mOsmol/kg); physiological (or isotonic) solutions have an osmolality similar to the osmolality of the body (about 275-295 mOsmol/kg), hypotonic solutions have an osmolality lower than the body (below about 250 mOsmol/kg) which actively promotes fluid absorption.

The pharmaceutical compositions according to the invention may be used as a medicament.

The pharmaceutical compositions according to the invention are suitable for i.v. administration; and may be suitable for alternative parenteral administration routes such as subcutaneous, or intra-muscular administration; or when transformed to an aerosol, for inhaled administration.

The pharmaceutical compositions according to the invention may especially be used for the preparation of a medicament, and/or are especially suitable, for use in the treatment of ulcer, digital ulcer, diabetic gangrene, diabetic foot ulcer, pressure ulcer (bedsore), hypertension, pulmonary hypertension, pulmonary arterial hypertension, Fontan disease and pulmonary hypertension associated with Fontan disease, sarcoidosis and pulmonary hypertension associated with sarcoidosis, peripheral circulatory disturbance (e.g., chronic arterial occlusion, intermittent claudication, peripheral embolism, vibration syndrome, Raynaud's disease), connective tissue disease (e.g., systemic lupus erythematosus, scleroderma, mixed connective tissue disease, vasculitic syndrome), reocclusion/restenosis after percutaneous transluminal coronary angioplasty (PTCA), arteriosclerosis, thrombosis (e.g., acute-phase cerebral thrombosis, pulmonary embolism), transient ischemic attack (TIA), diabetic neuropathy, ischemic disorder (e.g., cerebral infarction, myocardial infarction), angina (e.g., stable angina, unstable angina), chronic kidney diseases including glomerulonephritis and diabetic nephropathy at any stage, allergy, bronchial asthma, restenosis after coronary intervention such as atherectomy and stent implantation, thrombocytopenia by dialysis, the diseases in which fibrosis of organs or tissues is involved [e.g., renal diseases such as tubulointerstitial nephritis), respiratory diseases (e.g., interstitial pneumonia, (idiopathic) pulmonary fibrosis, chronic obstructive pulmonary disease), digestive diseases (e.g., hepatocirrhosis, viral hepatitis, chronic pancreatitis and scirrhous stomachic cancer), cardiovascular diseases (e.g., myocardial fibrosis), bone and articular diseases (e.g., bone marrow fibrosis and rheumatoid arthritis), skin diseases (e.g., cicatrix after operation, scalded cicatrix, keloid, and hypertrophic cicatrix), obstetric diseases (e.g., hysteromyoma), urinary diseases (e.g., prostatic hypertrophy), other diseases (e.g., alzheimer's disease, sclerosing peritonitis, type I diabetes and organ adhesion after operation)], erectile dysfunction (e.g., diabetic erectile dysfunction, psychogenic erectile dysfunction, psychotic erectile dysfunction, erectile dysfunction associated with chronic renal failure, erectile dysfunction after intrapelvic operation for removing prostata, and vascular erectile dysfunction associated with aging and arteriosclerosis), inflammatory bowel disease (e.g., ulcerative colitis, Crohn's disease, intestinal tuberculosis, ischemic colitis and intestinal ulcer associated with Behcet disease), gastritis, gastric ulcer, ischemic ophthalmopathy (e.g., retinal artery occlusion, retinal vein occlusion, ischemic optic neuropathy), sudden hearing loss, avascular necrosis of bone, intestinal damage caused by administration of a non-steroidal anti-inflammatory agent and symptoms associated with lumbar spinal canal stenosis.

The pharmaceutical compositions according to the invention may in particular be used for the preparation of a medicament, and/or are especially suitable, for use in the treatment of ulcer, digital ulcer, diabetic gangrene, diabetic foot ulcer, pulmonary hypertension, pulmonary arterial hypertension, Fontan disease and pulmonary hypertension associated with Fontan disease, sarcoidosis and pulmonary hypertension associated with sarcoidosis, peripheral circulatory disturbance (e.g. intermittent claudication, Raynaud's disease), connective tissue disease (e.g. systemic lupus erythematosus, scleroderma), chronic kidney diseases including glomerulonephritis and diabetic nephropathy at any stage, diseases in which fibrosis of organs or tissues is involved [e.g., renal diseases such as tubulointerstitial nephritis), or respiratory diseases (e.g., (usual) interstitial pneumonia/(idiopathic) pulmonary fibrosis)].

An aqueous (e.g. reconstituted, or reconstituted and further diluted) pharmaceutical composition is considered physically "stable", if during a certain period of time at least 80%, preferably at least 90% and most preferably at least 95% of the initial content of the COMPOUND is maintained over said period of time in a solubilized state.

A lyophilized composition (i.e. a lyophilized cake) is considered physically "stable", if during a certain period of time variations of less than 30%, preferably less than 20% and most preferably less than 10% with regard to reconstitution time and/or residual moisture are observed. Additionally, the cake appearance may be considered as criterion to determine physical stability of a lyophilized composition.

A pharmaceutical composition is considered chemically "stable", if under certain conditions and during a certain period of time at least 80%, notably at least 95%, especially at least 98%, and preferably at least 99% of the initial content of COMPOUND is maintained under said conditions and over said period of time without degradation. Especially degradation may be defined as degradation producing less than 1%, preferably less than 0.5%, of 2-(4-((5,6-diphenylpyrazin-2-yl)(isopropyl)amino) butoxy) acetic acid (i.e. the product resulting from hydrolysis of COMPOUND) under the specified conditions and during the specified period.

Furthermore, in particular for any aqueous pharmaceutical composition, chemical stability under exposure to light (measured e.g. by using an OSRAM L58W/840 lamp at a distance of 65 cm) may be considered in addition. The above values defining chemical stability are in absence of additional exposure to light.

Preferably, the lyophilized pharmaceutical compositions of this invention will be chemically and physically "stable" for at least 6, preferably for at least 12 months when kept at a temperature of 5° C. to 50° C. and a rH of about 75% or below. More preferably, they will be stable for at least 6 or preferably for 12 months when kept at a temperature of 15° C. to 45° C. and a rH of about 75% or below. Most preferred, they will be stable for at least 6 or preferably for 12 months when kept at a temperature of 25° C. to 40° C. and a rH of about 75% or below, especially at 40° C. and 75% rH, or in particular at 25° C. and 60% rH.

Preferably, the aqueous pharmaceutical compositions (e.g. the aqueous composition prior to lyophilization, the reconstituted formulation, or the reconstituted and further diluted formulation) of this invention will be chemically and physically "stable" for at least 6 hours, preferably for at least 12 hours when kept at a temperature of 5° C. to 50° C. More preferably, they will be stable for at least 6 or preferably for 12 hours when kept at a temperature of 15° C. to 45 C. Most preferred, they will be stable for at least 6 or preferably for 12 hours when kept at a temperature of 25° C. to 40° C., especially at room temperature.

The chemical stability of the pharmaceutical compositions may be tested in conventional manner, e.g. by measurement of the COMPOUND and its degradation products (such as especially 2-(4-((5,6-diphenylpyrazin-2-yl)(isopropyl)amino) butoxy) acetic acid). The content of COMPOUND and its degradation products may be evaluated via conventional HPLC.

The physical stability of the pharmaceutical compositions may be tested in conventional manner, e.g. by measurement of reconstitution time; water content; appearance and/or microscopy of the lyophilized composition (i.e. a lyophilized cake), e.g. after storage at a certain temperature and relative humidity for defined periods of time; and by measurement of the ability of the aqueous formulation (e.g. the aqueous composition prior to lyophilization, the reconstituted formulation, or the reconstituted and further diluted formulation) to maintain drug solubilization and to prevent precipitation after storage at a certain temperature for defined periods of time.

The aqueous pharmaceutical composition according to any one of embodiments 1) to 6) may be formulated in containers. For example from a batch size corresponding to 500 mg of COMPOUND (batch size of 1 kg of pharmaceutical composition), may lead to 250 vials of about 3.8 g of pharmaceutical composition per vial, and may be composed as follows:

| Material | Function | Percentage (% w/w) | Unit Dose (g) |
|---|---|---|---|
| water for injection (WFI) | solvent | 80 | 800 |
| aqueous sodium hydroxide solution (15 ww %) | buffer (base) | 0.316 | 3.16 |
| COMPOUND | Active ingredient | 5.00 | 0.500 |
| polysorbate 20 (10 ww % aqueous stock solution) | Excipient: Detergent | 3 | 30.00 |
| glycine | Excipient: bulking agent | 5 | 50.00 |
| aqueous phosphoric acid (85 ww %) | buffer (acid) | 0.1153 | 1.153 |
| aqueous sodium hydroxide solution (1 ww %) | buffer (base) | variable, adjust to pH 7.5 | variable, adjust to pH 7.5 |
| WFI | solvent | variable to adjust to a total of 100 | variable to adjust to a total of 1000 |
| Total | | 100.000 | 1000 |

The amounts may be adjusted for the purity of the respective ingredient, which may give rise to increased amounts of COMPOUND.

The process for the preparation of a lyophilized pharmaceutical composition as described before and filled in a container according to the present invention, may comprise the following steps:

Mix the amount of COMPOUND: target value: 0.500 g (e.g. in a 1500 mL glass beaker); with the respective amounts of WFI: target value: 800 g; glycine: target value: 50.00 g; 10% (w/w) polysorbate 20: target value: 30.00 g; 15% (w/w) NaOH: target value: 3.16 g; and phosphoric acid, 85% (w/w): target value: 1.153 g;

Stir to homogeneity.

Adjust the pH to pH 7.5 using 1.0% (w/w) NaOH.

Add WFI to target weight: 1000 g.

Filter (e.g. under laminar flow condition through a 0.22 µm PVDF membrane filter).

Fill vials (e.g. under laminar flow condition): Target fill weight: 3.80 g±3%.

The process for the lyophilization of the above pharmaceutical composition may for example comprise the following steps:

| Step | | Shelf temp. | Ice condenser temp. | Pressure | Time step | Cumulative time |
|---|---|---|---|---|---|---|
| # | Description | [° C.] | [° C.] | [mbar] | [h:min] | [h:min] |
| 1 | Loading | 20 | — | atm | 00:01 | 00:01 |
| 2 | Freezing, ramp | −45 | — | atm | 01:05 | 01:06 |
| 3 | Freezing | −45 | — | atm | 01:30 | 02:36 |
| 4 | Annealing, ramp | −3 | — | atm | 00:40 | 03:16 |
| 5 | Annealing | −3 | — | atm | 02:00 | 05:16 |
| 6 | Annealing, ramp | −45 | — | atm | 00:40 | 05:56 |
| | Freezing | −45 | −70 | atm | 00:30 | 06:26 |
| 7 | Vacuum Adjustment | −45 | −70 | 0.5 | 00:30 | 06:56 |
| 8 | Primary Drying, ramp | 35 | −70 | 0.5 | 02:00 | 08:56 |
| 9 | Primary Drying | 35 | −70 | 0.5 | 05:00 | 13:56 |
| 10 | Secondary Drying | 35 | −70 | 0.5 | 05:00 | 18:56 |
| 13 | Closing | 35 | −70 | 800 | 00:10 | 19:06 |

An alternative process for the lyophilization of the above pharmaceutical composition may for example comprise the following steps:

| Step | | Shelf temp. | Ice condenser temp. | Pressure | Time step | Cumulative time |
|---|---|---|---|---|---|---|
| # | Description | [° C.] | [° C.] | [mbar] | [h:min] | [h:min] |
| 1 | Loading | 20 | — | atm | 00:01 | 00:01 |
| 2 | Freezing, ramp | −45 | — | atm | 01:05 | 01:06 |
| 3 | Freezing | −45 | — | atm | 01:30 | 02:36 |
| 4 | Annealing, ramp | −3 | — | atm | 00:40 | 03:16 |
| 5 | Annealing | −3 | — | atm | 02:00 | 05:16 |
| 6 | Annealing, ramp | −45 | — | atm | 00:40 | 05:56 |
| | Freezing | −45 | −70 | atm | 00:30 | 06:26 |
| 7 | Vacuum Adjustment | −45 | −70 | 0.5 | 00:30 | 06:56 |
| 8 | Primary Drying, ramp | 35 | −70 | 0.5 | 03:00 | 09:56 |
| 9 | Primary Drying | 35 | −70 | 0.5 | 11:00 | 20:56 |
| 10 | Secondary Drying | 35 | −70 | 0.5 | 05:00 | 25:56 |
| 13 | Closing | 35 | −70 | 800 | 00:10 | 26:06 |

The annealing step (steps 4 to 6) in the above process is optional. A process comprising an annealing step may prevent shrinkage in the bottom region of the cake, as well as lid formation of the cake.

A further alternative process for the lyophilisation of the above pharmaceutical composition may for example comprise the following steps:

| Step | | Shelf temp. | Ice condenser temp. | Pressure | Time step | Cumulative time |
|---|---|---|---|---|---|---|
| # | Description | [° C.] | [° C.] | [mbar] | [h:min] | [h:min] |
| 1 | Loading | 20 | — | atm | 00:01 | 00:01 |
| 2 | Freezing, ramp | −45 | — | atm | 01:05 | 01:06 |
| 3 | Freezing | −45 | — | atm | 01:30 | 02:36 |
| 4 | Annealing, ramp | −3 | — | atm | 00:40 | 03:16 |

-continued

| # | Step Description | Shelf temp. [° C.] | Ice condenser temp. [° C.] | Pressure [mbar] | Time step [h:min] | Cumulative time [h:min] |
|---|---|---|---|---|---|---|
| 5 | Annealing | −3 | — | atm | 02:00 | 05:16 |
| 6 | Annealing, ramp | −45 | — | atm | 00:40 | 05:56 |
|   | Freezing | −45 | −70 | atm | 00:30 | 06:26 |
| 7 | Vacuum Adjustment | −45 | −70 | 0.5 | 00:30 | 06:56 |
| 8 | Primary Drying, ramp | 35 | −70 | 0.5 | 06:00 | 12:56 |
| 9 | Primary Drying | 35 | −70 | 0.5 | 11:00 | 23:56 |
| 10 | Secondary Drying | 35 | −70 | 0.5 | 05:00 | 28:56 |
| 13 | Closing | 20 | −70 | 800 | 00:10 | 29:06 |

In other words, the closing temperature may be a fifth temperature, with respect to embodiment 7), namely about 20° C. Again, the annealing step (steps 4 to 6) in the above process is optional. A process comprising an annealing step may prevent shrinkage in the bottom region of the cake, as well as lid formation of the cake.

Following the process for the lyophilization of the above pharmaceutical composition the vials may be sealed for example by crimping using the following process:

Place caps onto each vial and crimp e.g. with a semi- or fully automatic crimping machine, or equivalent.

The lyophilized pharmaceutical composition may be reconstituted by using the following process:

Adding saline or WFI (e.g. target value 8.1 mL) and shake gently until the cake is fully dissolved.

EXAMPLES

Abbreviations (as Used Herein and in the Description Above):
aq. aqueous
atm atmospheric pressure
DSC differential scanning calorimetry
HPLC high performance liquid chromatography
min minute(s)
poloxamer 188 polyoxypropylene-polyoxyethylene copolymer, e.g. Kolliphor® P188
PS20 polysorbate 20, e.g. Tween® 20
PS80 polysorbate 80, e.g. Tween® 80
rH relative humidity
RP reversed phase
RT room temperature
WFI water for injection Raw materials were purchased from commercial suppliers:

| Substance | Supplier/ Manufacturer | Cat. No. |
|---|---|---|
| Octane-1-sulphonic acid sodium, salt 98%) | Carl Roth GmbH | KK55.2 |
| Purified water ≤0.2 μmS/cm, <10 ppb TOC) | — | |
| Saline for infusion, 0.9 % | B Braun | 6726174 |
| o-Phosphoric acid, 85% | Merck KGaA | 1.00563.1000 |
| Methanol, ROTISOLVO® HPLC Gradient | Carl Roth GmbH | 4627.2 |
| Sodium hydroxide, ≥98 %, (Ph. Eur., USP, BP, in pellets) | Carl Roth GmbH | P031 |
| Kolliphor® P 188, Poloxamer, Ph EUR | BASF | 50259527 |
| Tween® 20 EMPROVE® (exp Ph. Eur. JPE ,NF) | Merck Chemicals | 8.17072.1000 |
| Tween® 80, EMPROVE (exp, Ph. Eur., JP, NF) | Merck Chemicals | 8.17061.1000 |
| Glycine, (≥98.5% Ph. Eur) | Carl Roth GmbH | T873 |
| Trehalose dehydrate, 100 PH | Hayashibara | 33016 |
| Kollidon® 17 PF, Polyvinylpyrrolidone Material | BASF | 51598188 |
| RP-HPLC column | phenomenex | CH0-3387 |
| Amber glass HPLC vials | WICOM Germany GmbH | WIC 42720 |
| 10R glass vials, type I FIOLAX | Nipro Glass Germany | MG037-002-0049-086 |
| Lyo stopper 20 mm, 1319 4023 | West Pharmaceutical | 7002-2716 |
| Syringe Luer-Lok, amber | BD Plastipak™ | 300869 |
| Infusion tubing | Cair LGL | P03115B |
| PVDF syringe filter, 0.22 μm | Merck Millipore Ltd. | SLGUM33RS |
| Millex ®-GV syringe filter unit, 33 mm 0.22 μm, PVDF membrane | Merck Millipore Ltd. | SLGV033RS |
| Luer Lock Combi-Stopper | Braun | 4495101 |
| Silicone tube for sterile filtration, thickness 1.6 mm, inner-Ø 3.2 mm, outer-Ø 6.4 mm | Carl Roth GmbH | CH26.1 |
| PD-Tips for multistep pipette | Brand ® | 702382 |

The following apparatuses were used:
HPLC Equipment
  Manufacturer: Agilent Technologies (Santa Clara, CA, USA)
  Type: 1100 Series
  Degasser: G1322A
  BinPump: G1312A
  ALS: G1329A
  ALSTherm: G1330A
  ColCom: G1316A
  VWD: G1314A
  Chromatography management software: Dionex, Chromeleon 6.80
    Agilent, Chemstation B.04.03 SP1
    Wyatt, Astra 6.1
  UV Spectrophotometer: Agilent Technologies Cary 50;
Purified water supply: Siemens Ultra Clean UV UF TM; pH meter: Mettler Toledo SevenMulti; Electrode: InLab Micro;
Balance: Kern EW 6200-2NM
Preparation of Compound:
  The preparation of selexipag (COMPOUND: 2-{4-[N-(5,6-diphenylpyrazin-2-yl)-N-isopropylamino]butyloxy}-N-(methylsulfonyl)acetamide) is described in WO2002/088084. The preparation of polymorphic forms, i.e. the crystalline forms I, II, and III of the free base is disclosed in WO2010/150865; polymorphic forms of pharmaceutically acceptable salts are disclosed in WO2011/024874. COMPOUND was used in the following Examples and assays in form of the free base, especially crystals of polymorphic form I.
Analytical Methods
Differential Scanning Calorimetry (DSC)
  The thermal properties of the frozen bulk drug product solution are evaluated by differential scanning calorimetry.

By DSC phase transition temperatures (i.e. crystallization- and melting point) can be identified by measuring the behavior of the sample when cooled down/heated up compared to an empty reference pan. When an endothermic reaction like melting occurs the system has to put more energy into the sample than into the reference to keep both on the same temperature level. This required power is measured and used for the calculation of the phase transition temperature and enthalpy.

The phase transition temperatures of compositions prior to lyophilization are determined by differential scanning calorimetry using a DSC-8000 (Perkin Elmer, Waltham, MA, USA). Approx. 20 mg of the corresponding solution is weighted into a 50 μL aluminum sample pan. The pan is sealed with a closed aluminum DSC-cover. An empty aluminum sample pan is used as reference. The following cycle is performed:

| Step | Start temp | End temp | Scanning rate | Duration |
|---|---|---|---|---|
| Equilibration | 25° C. | 25° C. | — | 1 min |
| 1$^{st}$ cooling step | 25° C. | −65° C. | 10° C./min | 9 min |
| Equilibration | −65° C. | −65° C. | — | 1 min |
| 1$^{st}$ heating step | −65° C. | 25° C. | 10° C./min | 9 min |
| Equilibration | 25° C. | 25° C. | — | 1 min |
| 2$^{nd}$ cooling step | 25° C. | −65° C. | 10° C./min | 9 min |
| Equilibration | −65° C. | −65° C. | — | 1 min |
| 2$^{nd}$ heating step | −65° C. | 25° C. | 10° C./min | 9 min |

Evaluation of the melting point is performed in the second heating step.

Reversed Phase HPLC for Content and Purity Analysis

RP-HPLC is used to quantify COMPOUND in the lyophilized compositions and to separate COMPOUND from potential impurities in order to rate the product purity. RP-HPLC measurements are converted by calculation into COMPOUND concentration in the respective sample.

Chromatographic Parameters

Mobile phase: 3.24 g octane-1-sulphonic acid sodium salt are dissolved in 1500 mL purified water. 1.5 mL of o-phosphoric acid 85% are added. 3500 mL methanol are added.

Flow rate: 1.0 mL/min isocratic

Temperature: 40° C.

VWD: 302 nm

Injection volume: 10 μL

Sample temperature: 10° C.

Run time: 40 min

Reference Solution and Calibration Curve

Diluent: 70% methanol, 30% purified water (v/v)

Standard stock solution (100 μg/mL COMPOUND):

A 200 mL volumetric brown glass vessel is filled with 180 mL of diluent. Subsequently 20 mg of COMPOUND reference material are added. The mixture is treated in an ultra sound bath for 10 minutes at 20° C. The volume is filled up to 200 mL after complete dissolution of COMPOUND.

Standard solution (5 μg/mL): Standard stock solution (100 μg/mL) is diluted 1:20 (v/v) using diluent.

Calibration Curve:

Five different injection volumes of the reference solution (5 μg/mL) are applied to the column in equidistant steps (i.e. 5 μL, 10 μL, 15 μL, 20 μL and 25 μL) at the beginning and at the end of each analysis sequence. The detected peak areas are aligned with the respective applied masses and a formula for conversion of UV-measured responses into COMPOUND mass is generated by linear regression of the mean values.

Sample Preparation

Diluent: 70% methanol, 30% purified water (v/v).

Prior to analysis, samples were diluted to a concentration of 10 μg/mL using diluent or they were used undiluted if the concentration was below 10 μg/mL.

Karl-Fischer Titration for Residual Moisture Analysis 50-100 mg of three random vials of each lyophilization cycle are weighed into a glass vial which is sealed with a crimp cap. The sample is transferred into the oven of the Karl Fischer coulometer (756/774; Metrohm) which is heated to 100° C. The septum of the cap is penetrated by an injection needle, and the generated water vapor is directly transferred into the titration chamber of the Karl Fischer coulometer by dry nitrogen flow. Empty glass vials are used for blank correction.

Visual Appearance

Photographs are made of exemplary vials after each lyophilization cycle.

Lyophilizates are removed from the vial by carefully breaking the glass vial and the lyophilized cake is cut vertically to screen its inner layer for collapse zones.

Scanning Electron Microscopy (SEM)

Lyophilizates are analyzed by SEM to evaluate their microstructure. The respective lyophilizates are carefully cut and the vertical cross sections as well as the top/bottom surfaces are analyzed via SEM.

Example 1

A batch size corresponding to 500 mg of COMPOUND (batch size of 1 kg of pharmaceutical composition), leading to 250 vials of about 3.8 g of pharmaceutical composition per vial, was composed and prepared as follows:

| Material | Function | Percentage (% w/w) | Unit Dose (g) |
|---|---|---|---|
| water for injection (WFI) | solvent | 80 | 800 |
| aqueous sodium hydroxide solution (15 ww %) | buffer (base) | 0.316 | 3.16 |
| COMPOUND | Active ingredient | 5.00 | 0.500 |
| polysorbate 20 (10 ww % aqueous stock solution) | Excipient: Detergent | 3 | 30.00 |
| glycine | Excipient: bulking agent | 5 | 50.00 |
| aqueous phosphoric acid (85 ww %) | buffer (acid) | 0.1153 | 1.153 |

-continued

| Material | Function | Percentage (% w/w) | Unit Dose (g) |
|---|---|---|---|
| aqueous sodium hydroxide solution (1 ww %) | buffer (base) | variable, adjust to pH 7.5 | variable, adjust to pH 7.5 |
| WFI | solvent | variable to adjust to a total of 100 | variable to adjust to a total of 1000 |
| | Total | 100.000 | 1000 |

Fill the amount of WFI in a 1500 mL glass beaker: Target value: 800 g.
Add the amount of 15% (w/w) NaOH: Target value: 3.16 g.
Stir to homogeneity.
Add the amount of COMPOUND: Target value: 0.500 g.
Stir to homogeneity.
Add the amount of glycine: Target value: 50.00 g.
Stir to homogeneity.
Add the amount of 10% (w/w) polysorbate 20: Target value: 30.00 g.
Stir to homogeneity.
Add the amount of phosphoric acid, 85% (w/w): Target value: 1.153 g.
Stir to homogeneity.
Adjust the pH to pH 7.5 using 1.0% (w/w) NaOH.
Add WFI to target weight: 1000 g.
Filter under laminar flow condition through a 0.22 μm PVDF membrane filter.
Fill vials under laminar flow condition: Target fill weight: 3.80 g±3%.
The vials were lyophilized using the following procedure:

| Step | | Shelf temp. [° C.] | Ice condenser temp. [° C.] | Pressure [mbar] | Time step [h:min] | Cumulative time [h:min] |
|---|---|---|---|---|---|---|
| # | Description | | | | | |
| 1 | Loading | 20 | — | atm | 00:01 | 00:01 |
| 2 | Freezing, ramp | −45 | — | atm | 01:05 | 01:06 |
| 3 | Freezing | −45 | — | atm | 01:30 | 02:36 |
| 4 | Annealing, ramp | −3 | — | atm | 00:40 | 03:16 |
| 5 | Annealing | −3 | — | atm | 02:00 | 05:16 |
| 6 | Annealing, ramp | −45 | — | atm | 00:40 | 05:56 |
| | Freezing | −45 | −70 | atm | 00:30 | 06:26 |
| 7 | Vacuum Adjustment | −45 | −70 | 0.5 | 00:30 | 06:56 |
| 8 | Primary Drying, ramp | 35 | −70 | 0.5 | 02:00 | 08:56 |

-continued

| Step | | Shelf temp. [° C.] | Ice condenser temp. [° C.] | Pressure [mbar] | Time step [h:min] | Cumulative time [h:min] |
|---|---|---|---|---|---|---|
| # | Description | | | | | |
| 9 | Primary Drying | 35 | −70 | 0.5 | 05:00 | 13:56 |
| 10 | Secondary Drying | 35 | −70 | 0.5 | 05:00 | 18:56 |
| 13 | Closing | 35 | −70 | 800 | 00:10 | 19:06 |

Following the process for the lyophilization of the above pharmaceutical composition the vials were sealed by crimping using the following process:

Place caps onto each vial and crimp e.g. with a semi- or fully automatic crimping machine.

Example 2

A batch size of 60 vials of the following composition (corresponding to 0.50 mg/g COMPOUND, 5 ww % glycine, 0.3 ww % polysorbate 20 in 10 mmol/kg sodium phosphate buffer, pH 7.5) was prepared:

| | | | |
|---|---|---|---|
| a | WFI | 3200 mg | 3200 mg |
| b | NaOH, 15% (w/w) | 12.0 mg | 12.0 mg |
| c | COMPOUND | 1.90 mg | — |
| d | glycine | 190 mg | 190 mg |
| e | H3PO4, 85% (w/w) | 4.38 mg | 4.38 mg |
| f | polysorbate 20, 10% (w/w) | 11.4 mg | 11.4 mg |
| g | NaOH, 1% (w/w) | adj. of pH 7.5 ± 0.2 | adj. of pH 7.5 ± 0.2 |
| h | WFI | ad to 3800 mg final weight | ad.to 3800 mg final weight |

1. Fill a) in a compounding vessel
2. Add b) under agitation
3. Add c) under agitation to obtain a clear solution in the absence of light
4. Add d) under agitation to obtain a clear solution
5. Add e) under agitation
6. Add f) under agitation
7. Adjust pH with g) (target: pH 7.5)
8. Fill up with h) to a final weight of 3.800 mg
9. Double check of target pH 60 vials were processed using the above procedure.

The vials were lyophilized using the following procedures:

A: Process Parameters of a Lyophilization Run Using 0.85 Mbar Vacuum.

| # | Step Description | Shelf temperature [° C.] | Ice condenser temperature [° C.] | Pressure [mbar] | Time step [h:min] | Cumulative time [h:min] |
|---|---|---|---|---|---|---|
| 1 | Loading | 20 | — | atm | 00:01 | 0:01 |
| 2 | Freezing ramp | −5 | — | atm | 00:25 | 0:26 |
| 3 | Freezing | −5 | — | atm | 01:00 | 1:26 |
| 4 | Freezing ramp | −45 | — | atm | 00:40 | 2:06 |
| 5 | Freezing | −45 | — | atm | 06:00 | 8:06 |
| 6 | Vacuum adjustment | −45 | −70 | 0.85 | 00:30 | 8:36 |
| 7 | Primary Drying ramp | 35 | −70 | 0.85 | 02:00 | 10:36 |
| 8 | Primary Drying | 35 | −70 | 0.85 | 25:00 | 35:36 |
| 9 | Secondary Drying | 35 | −70 | 0.85 | 15:00 | 50:36 |

Visual inspection revealed lyophilized cakes with slight shrinkage at the bottom region and top surfaces (also referred to as lids) showing a denser structure probably causing the shrinkage/increased density at the bottom region due to cake resistance.

Analysis of Lyophilized Cake:

The residual water content (Karl-Fischer) was 0.41%.

For COMPOUND content and purity in the lyophilized drug product two random vials were reconstituted with 3.6 mL saline. The reconstituted solutions were diluted 1:50 using diluent and subsequently analyzed by RP-HPLC:

COMPOUND content (target value=0.50 mg/mL): 0.54 mg/mL; COMPOUND purity: 100%

B: Process Parameters of a Lyophilization Run Using 0.5 Mbar Vacuum.

| # | Step Description | Shelf temperature [° C.] | Ice condenser temperature [° C.] | Pressure [mbar] | Time step [h:min] | Cumulative time [h:min] |
|---|---|---|---|---|---|---|
| 1 | Loading | 20 | — | atm | 00:01 | 0:01 |
| 2 | Freezing ramp | −5 | — | atm | 00:25 | 0:26 |
| 3 | Freezing | −5 | — | atm | 01:00 | 1:26 |
| 4 | Freezing ramp | −45 | — | atm | 00:40 | 2:06 |
| 5 | Freezing | −45 | — | atm | 01:30 | 3:36 |
| 6 | Vacuum adjustment | −45 | −70 | 0.50 | 00:30 | 4:06 |
| 7 | Primary Drying ramp | 35 | −70 | 0.50 | 02:00 | 6:06 |
| 8 | Primary Drying | 35 | −70 | 0.50 | 20:00 | 26:06 |
| 9 | Secondary Drying | 35 | −70 | 0.50 | 10:00 | 36:06 |

Visual inspection revealed lyophilized cakes with formation of a dense lid as well as shrinkage in the bottom region.

Analysis of Lyophilized Cake:

The residual water content (Karl-Fischer) was 0.50%.

For COMPOUND content and purity in the lyophilized drug product two random vials were reconstituted with 3.6 mL saline. The reconstituted solutions were diluted 1:50 using diluent and subsequently analyzed by RP-HPLC:

COMPOUND content (target value=0.50 mg/mL): 0.52 mg/mL; COMPOUND purity: 100%

C: Process Parameters of a Lyophilization Run Including an Annealing Step.

| # | Step Description | Shelf temperature [°C.] | Ice condenser temperature [°C.] | Pressure [mbar] | Time step [h:min] | Cumulative time [h:min] |
|---|---|---|---|---|---|---|
| 1 | Loading | 20 | — | atm | 00:01 | 0:01 |
| 2 | Freezing ramp | −45 | — | atm | 01:00 | 1:01 |
| 3 | Freezing | −45 | — | atm | 01:30 | 2:31 |
| 4 | Annealing ramp | −3 | — | atm | 00:40 | 3:11 |
| 5 | Annealing | −3 | — | atm | 02:00 | 5:11 |
| 6 | Annealing ramp | −45 | — | atm | 00:40 | 5:51 |
| 7 | Freezing | −45 | — | atm | 00:30 | 6:21 |
| 8 | Vacuum adjustment | −45 | −70 | 0.50 | 00:30 | 6:51 |
| 9 | Primary Drying ramp | 35 | −70 | 0.50 | 02:00 | 8:51 |
| 10 | Primary Drying | 35 | −70 | 0.50 | 10:00 | 18:51 |
| 11 | Secondary Drying | 35 | −70 | 0.50 | 10:00 | 28:51 |

Visual inspection revealed lyophilized cakes with no shrinkage in the bottom region of the cake and no the lid formation.

Analysis of Lyophilized Cake:
  residual water (Karl-Fischer): 0.20%
  COMPOUND content (target value=0.50 mg/mL): 0.51 mg/mL
  COMPOUND purity: 100%

The residual water content was significantly reduced by the annealing step to 0.20%.

Example 3

In analogy to Example 2, a batch size of 60 vials of the following composition (corresponding to 0.50 mg/g COMPOUND, 5 ww % glycine, 0.1 ww % polysorbate 20 in 10 mmol/kg sodium phosphate buffer, pH 7.5) was prepared:

| a | WFI | 3200 mg | 3200 mg |
|---|---|---|---|
| b | NaOH, 15% (w/w) | 12.0 mg | 12.0 mg |
| c | COMPOUND | 1.90 mg | — |
| d | glycine | 190 mg | 190 mg |
| e | H3PO4, 85% (w/w) | 4.38 mg | 4.38 mg |
| f | polysorbate 20, 10% (w/w) | 38.0 mg | 3.80 mg |
| g | NaOH, 1 % (w/w) | adj. of pH 7.5 ± 0.2 | adj. of pH 7.5 ± 0.2 |
| h | WFI | ad to 3800 mg final weight | ad to 3800 mg final weight |

Compositions of Example 3 were subjected to lyophilization conditions as described in Example 2 A) to C).

Visual examination revealed lyophilized cakes not different from the respective cakes obtained for the compositions of Example 2 under the same conditions.

Example 4: In-Use Stability Testing

To evaluate potential adsorption of COMPOUND to the infusion set, the following procedure was applied:

Preparation of a simulated infusion solution in 0.9% NaCl with COMPOUND content of 4.5 µg/mL and 36 µg/mL, respectively, by direct mixing in the syringe:

The respective lyophilizate was reconstituted in 3.6 mL saline (resulting in approx. 3.8 mL total volume with a COMPOUND concentration of 0.5 mg/mL), the COMPOUND concentration was evaluated by RP-HPLC (sampling point 1). The plunger of the 50 mL PP amber syringe was removed and the syringe was closed by a luer lock combi cap. For 4.5 µg/mL COMPOUND: 49.55 g of 0.9% NaCl (density at 25° C.=1.003 g/mL) was filled in the 50 mL syringe. For 36 µg/mL COMPOUND: 46.40 g of 0.9% NaCl (density at 25° C.=1.003 g/mL) was filled in the 50 mL syringe.

For 4.5 µg/mL COMPOUND: 0.450 mL of the reconstituted formulation variant (0.5 mg/mL COMPOUND) was taken out of the 10R glass vial and transferred into the 50 mL PP syringe filled with saline to obtain a COMPOUND concentration for infusion of 4.5 µg/mL. For 36 µg/mL COMPOUND: 3.6 mL of the reconstituted formulation variant (0.5 mg/mL COMPOUND) was taken out of the 10R glass vial and transferred into the 50 mL PP syringe filled with saline to obtain a COMPOUND concentration for infusion of 36 µg/mL. The syringe was closed by inserting the plunger. The solution was homogeneously mixed by gentle shaking. The overpressure in the syringe was released by careful opening of the closure cap in up-right position. The syringe was stored for 4 hours (as a worst case) at room temperature and in absence of light. The infusion tubing was coupled to the syringe and flushed with the infusion solution. The first mL was collected (sampling point 2) and analyzed by RP-HPLC. The COMPOUND concentration and impurity profile was evaluated. After a total extraction time (testing an infusion flow of 0.625 mL/min) of 80 min at room temperature and in absence of light the remaining infusion solution was released and collected, the last 1 mL was sampled directly into an amber glass HPLC vial for analysis (sampling point 3). The COMPOUND concentration and impurity profile was evaluated. The total released infusion volume in the previous steps was collected and homogenized. The total volume was documented and the concentration of COMPOUND and impurity profile was determined using RP-HPLC (sampling point 4). All purity and content determination of COMPOUND in solution was done in duplicate by RP-HPLC using a standard curve.

For judgment of the total dose of COMPOUND delivered to the patient the COMPOUND contents measured at the different sampling points were added up in a total mass balance (sampling point 4). The relative total dose with reference (100%) to the measured COMPOUND concentration in the reconstituted vial is shown below:

| # | target pH | detergent | bulking agent | target COMPOUND concentration for infusion [μg/mL] | Relative total recovery of COMPOUND (sampling point 4) |
|---|---|---|---|---|---|
| 1a | 7.5 | 0.1% PS20 | 5% glycine | 4.5 | 90% |
| | | | | 36 | 97% |
| 2 | 7.5 | 0.1% poloxamer 188 | 5% glycine | 4.5 | 87% |
| | | | | 36 | 96% |
| 3 | 7.5 | 0.1% poloxamer 188 | 5% trehalose | 4.5 | 87% |
| | | | | 36 | 96% |
| 4 | 7.5 | 0.1% PS20 | 5% trehalose | 4.5 | 88% |
| | | | | 36 | 97% |
| 5 | 7.5 | 0.1% PS80 | 5% glycine | 4.5 | 83% |
| | | | | 36 | 97% |
| 1b | 7.5 | 0.3% PS20 | 5% glycine | 4.5 | 93%, 94% |

The relative reduction of COMPOUND content is higher in the higher diluted infusion solutions (4.5 μg/mL) than in the lower dilutions (36 μg/mL). With 4.5 μg/g COMPOUND, the highest decrease could be observed in variant #5; the lowest decrease in variant #1a. In the variants with 36 μg/g COMPOUND the adsorption to the infusion set was comparable in all tested variants with 3% to 4% loss of COMPOUND content.

The in-use stability test with 3-fold polysorbate 20 concentration in variant #1b with 4.5 μg/g COMPOUND yielded to a further improvement of 3-4 percentage points over the observed COMPOUND recovery of 90% in variant #1a with 0.1% polysorbate 20.

Example 5: Physical and Chemical Stability Testing

Buffer and Sample Preparation

Compound Stock Solution (1 mg/g COMPOUND in 10 Mmol/Kg Na—P04, pH 7.5 Via Pre-Dissolution in NaOH):

1680 mg of 4 M NaOH were topped with 500 g of purified water before 600 mg of COMPOUND were added. The mixture was stirred in a stainless steel beaker at room temperature for 60 min until a clear solution was obtained. 691.2 mg of o-phosphoric acid (85%) was added and the pH was adjusted to 7.5 using 1 M NaOH. Finally the solution was filled up with purified water to a final mass of 600 g.

Bulking Agent Stock Solutions (10% w/w Bulking Agent in 10 Mmol/Kg Na—PO4, pH 7.5):

287.5 mg o-phosphoric acid (85%) were topped with 75.0 g of purified water. 10.00 g of the respective bulking agent were added and the mixture was stirred until a clear solution was obtained. Subsequently the pH was adjusted to 7.5 using 1 M NaOH and the solution was filled up to a final mass of 100 g.

Detergent Stock Solutions (10% w/w Detergent in 10 mmol/kg Na—PO4, pH 7.5):

1.00 g of the respective detergent was filled up to 10.0 g with 10 mmol/kg Na—PO4, pH 7.5 and stirred until a clear solution was obtained.

Compounding and Aliquoting of the Formulation Variants for Lyophilization:

900 mg of the respective detergent stock solution, 45 g of the respective bulking agent stock solution, and 45 g of COMPOUND stock solution were mixed in a stainless steel beaker resulting in the respective formulation variant containing 0.5 mg/g COMPOUND, 5% (w/w) bulking agent and 0.1% (w/w) detergent in 10 mmol/kg sodium phosphate buffer at pH 7.5. Subsequently, the resulting solution was filtered through a 0.22 μm PVDF filter and filled into 10R vials by aliquots of 3.8 mL. The vials were sealed with a lyo stopper and a proper crimp cap.

The following samples were prepared:

| # | target pH | detergent | bulking agent |
|---|---|---|---|
| 6 | 7.5 | 0.1% poloxamer 188 | 5% glycine |
| 7 | 7.5 | 0.1% poloxamer 188 | 5% mannitol |
| 8 | 7.5 | 0.1% poloxamer 188 | 5% trehalose |
| 9 | 7.5 | 0.1% poloxamer 188 | 5% Kollidon ® 17PF |
| 10 | 7.5 | 0.1% poloxamer 188 | 5% L-proline |
| 11 | 7.5 | 0.1% PS20 | 5% glycine |
| 12 | 7.5 | 0.1% PS20 | 5% mannitol |
| 13 | 7.5 | 0.1% PS20 | 5% trehalose |
| 14 | 7.5 | 0.1% PS20 | 5% Kollidon ® 17PF |
| 15 | 7.5 | 0.1% PS20 | 5% L-proline |
| 16 | 7.5 | 0.1% PS80 | 5% glycine |
| 19 | 7.5 | 0.1% PS80 | 5% Kollidon ® 17PF |
| 20 | 7.5 | 0.1% PS80 | 5% L-proline |

A conservative lyophilization cycle was chosen that was considered to be suitable for all formulation variants. The annealing step was performed according to literature (Xi-aolin Tang and Michael J. Pikal, Pharmaceutical Research, Vol. 21, No. 2, February 2004).

| Step | Shelf temperature [° C.] | Ice condenser temperature [° C.] | Pressure (MKS) [mbar] | Time step [h:min] | Cumulative time [h:min] |
|---|---|---|---|---|---|
| Loading | 20 | — | 1000 | 00:01 | 0:01 |
| Freezing ramp | −45 | — | 1000 | 01:00 | 1:01 |
| Freezing | −45 | — | 1000 | 04:00 | 5:01 |
| Annealing ramp | −20 | — | 1000 | 01:00 | 6:01 |
| Annealing | −20 | — | 1000 | 03:00 | 9:01 |
| Freezing ramp | −45 | — | 1000 | 01:00 | 10:01 |
| Freezing | −45 | — | 1000 | 02:00 | 12:01 |
| Vacuum adjustment | −45 | −75 | 0.05 | 00:30 | 12:31 |
| Primary Drying ramp | −10 | −75 | 0.05 | 01:00 | 13:31 |
| Primary Drying | −10 | −75 | 0.05 | 50:00 | 63:31 |

-continued

| Step | Shelf temperature [° C.] | Ice condenser temperature [° C.] | Pressure (MKS) [mbar] | Time step [h:min] | Cumulative time [h:min] |
|---|---|---|---|---|---|
| Secondary Drying ramp | 40 | −75 | 0.05 | 03:00 | 66:31 |
| Secondary Drying | 40 | −75 | 0.05 | 05:00 | 71:31 |

Physical Stability:

The glycine (#6, #11, and #16) and mannitol (#7 and #12) containing variants showed almost no visible cake deformation. Trehalose containing variants (#8 and #13) showed slight shrinkage, whereby no cracks could be observed. The variants containing Kollidon® 17PF (#9, #14, and #19) showed strong shrinkage as well as cracked cakes. L-proline (#10, #15, and #20) was not suitable in these particular compositions. Despite the relatively low temperature level L-proline containing lyophilizates melted during the lyophilization process causing the sublimation pressure to push the cake upwards.

Chemical Stability:

Six different samples were taken of each formulation variant for content and purity analysis by RP-HPLC after the different preparation steps.

The purity of COMPOUND at different sampling times was determined by calculating the relative peak areas at 302 nm.

| # | before filtration | after filtration | after lyophilization before forced degradation | after 4 weeks 40° C. 75 % rH | after 4 weeks 60° C. uncontrolled rH |
|---|---|---|---|---|---|
| 6 | 100.0 | 100.0 | 99.5 | 100.0 | 98.9 |
| 7 | 100.0 | 100.0 | 99.2 | 99.5 | 81.9 |
| 8 | 100.0 | 100.0 | 99.3 | 99.5 | 98.3 |
| 9 | 99.6 | 99.7 | 96.7 | 95.7 | 95.9 |
| 10 | 100.0 | 100.0 | 98.5 | 99.4 | 93.7 |
| 11 | 100.0 | 100.0 | 99.3 | 99.9 | 98.8 |
| 12 | 100.0 | 100.0 | 98.8 | 99.2 | 80.7 |
| 13 | 100.0 | 99.9 | 99.2 | 99.5 | 98.0 |
| 14 | 100.0 | 99.9 | 97.1 | 96.6 | 96.0 |
| 15 | 100.0 | 100.0 | 99.5 | 99.4 | 87.2 |
| 16 | 100.0 | 100.0 | 99.7 | 99.9 | 98.7 |
| 19 | 99.9 | 99.8 | 97.8 | 97.5 | 97.6 |
| 20 | 100.0 | 100.0 | 99.6 | 99.4 | 87.1 |

During compounding, filtration and lyophilization COMPOUND was sufficiently stable in all formulation matrices: No significant decrease of content and purity was observed. The lyophilization process has no detectable impact on content and purity. The samples stored at 40° C. showed few to no reduction of content and purity. Exposure to elevated temperatures of the lyophilisates during the forced degradation study at 60° C. showed low stability for mannitol containing lyophilisates (#7, #12) and best chemical stability for the glycine (#6, #11, #16) and trehalose (#8, #13) containing variants.

Example 6: Adsorption Study

Reference Example 6a

Lyophilizates containing 0.1 mg/g of COMPOUND were prepared using the following composition at target pH of 7.5:

| Component | Quantity |
|---|---|
| COMPOUND | 0.1 g/kg |
| Sodium hydroxide aq. 1 M | 1.04 g/kg |
| Hydrochloric Acid aq. 1 M | 0.6 g/kg |
| Trometamol (2-Amino-2-hydroxymethyl-propane-1,3-diol) adjusted to pH 7.5 | 2.5 mM |
| Glycine | 25 g/kg |
| WFI | 973 g/kg |

Reference Example 6b

Lyophilizates containing 0.5 mg of COMPOUND in 20 mL amber vials were prepared using the following composition at target pH of 7.5:

| Component | Quantity per vial |
|---|---|
| COMPOUND | 0.5 mg |
| Sodium hydroxide aq. 1 M | 5.2 mg |
| Hydrochloric Acid aq. 1 M | 3.0 mg |
| Trometamol (2-Amino-2-hydroxymethyl-propane-1,3-diol) | 1.5 mg |
| Glycine | 125.0 mg |

The compositions were reconstituted in the vial with 20 mL of vehicle and optionally further diluted to % concentration of COMPOUND by directly diluting with further vehicle in the syringe.

Adsorption is tested by applying a flow rate of 0.3 mL/min in the infusion set. Concentrations of COMPOUND are measured in the lyophilization vial (reference value), [optionally: in the syringe following the dilution step ($T_s$)], at $T_0$ (first drops flowing out of the infusion set), and after 5 min ($T_5$) and 10 min ($T_{10}$) of flow through the infusion set.

a) The reconstituted composition 0.9% saline as vehicle (no further dilution) shows adsorption to the infusion set as follows:

| Time | recovery | Time | recovery | Time | recovery | Time | recovery |
|---|---|---|---|---|---|---|---|
| $T_s$ | not measured | $T_0$ | 59% | $T_5$ | 100% | $T_{10}$ | 100% |

Addition of 2 ww % PEG 400, 10 ww % ethanol, or 6% propylene glycol to the vehicle results in recovery at $T_0$ of 70%, 76%, 67%, respectively.

b) The reconstituted composition using i) 0.9% saline+40 ww % hydroxypropyl-beta-cyclodextrin, ii) 0.9% saline+3 ww % Kolliphor®, or iii) 0.9% saline+2 ww % Tween® 80, as vehicle (no further dilution) shows adsorption to the infusion set as follows:

| # | Time | recovery | Time | recovery | Time | recovery | Time | recovery |
|---|---|---|---|---|---|---|---|---|
| i) | $T_s$ | not measured | $T_0$ | 97% | $T_5$ | 102% | $T_{10}$ | 100% |
| ii) | $T_s$ | not measured | $T_0$ | 100% | $T_5$ | 105% | $T_{10}$ | 107% |
| iii) | $T_s$ | not measured | $T_0$ | 101% | $T_5$ | 106 % | $T_{10}$ | 104% | c) Testing the reconstituted composition using i) 0.9% saline+0.1 ww % Kolliphor®, or ii) 0.9% saline+0.1 ww %

Tween® 80, as vehicle with further dilution to ½ concentration of COMPOUND confirms that adsorption at $T_0$ can be prevented:

| # | Time | recovery | Time | recovery | Time | recovery | Time | recovery |
|---|---|---|---|---|---|---|---|---|
| i) | $T_s$ | 92% | $T_0$ | 93% | $T_5$ | 96% | $T_{10}$ | 96% |
| ii) | $T_s$ | 95% | $T_0$ | 95% | $T_5$ | 96% | $T_{10}$ | 96% |
| 0.9% saline | $T_s$ | 95% | $T_0$ | 36% | $T_5$ | 96% | $T_{10}$ | 95% |

In an absolute bioavailability study, a composition of reference example 6a, reconstituted with saline was used; and the adsorption was overcome by using concentrations above 8 µg/mL, flushing of the entire infusion set with the reconstituted composition of reference example 6a, and using low infusion rates, such as 0.1-0.3 mL/min.

The invention claimed is:

1. An aqueous pharmaceutical composition comprising:
   about 0.1 g/kg to 1 g/kg of the compound 2-{4-[N-(5,6-diphenylpyrazin-2-yl)-N-isopropylamino]butyloxy}-N-(methylsulfonyl)acetamide:

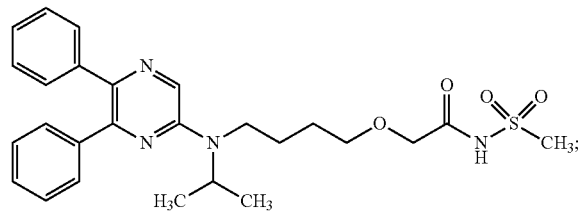 [SMILES: CC(C)N(CCCCOCC(=O)NS(C)(=O)=O)c1cnc(-c2ccccc2)c(-c2ccccc2)n1]

about 2.5 ww % to 10 ww % of a bulking agent which is glycine;
   about 0.05 ww % to 0.4 ww % of a detergent which is polysorbate 20; and
   an aqueous phosphate buffer, wherein the total amount of said phosphate buffer is about 5 mmol/kg to 20 mmol/kg;
   wherein the pH of said aqueous pharmaceutical composition is between about 7 and 8.

2. An aqueous pharmaceutical composition according to claim 1; comprising:
   about 0.5 g/kg of the compound: 2-{4-[N-(5,6-diphenylpyrazin-2-yl)-N-isopropylamino]butyloxy}-N-(methylsulfonyl)acetamide;
   about 3 ww % to 6 ww % of glycine;
   about 0.1 ww % to 0.3 ww % of polysorbate 20; and
   aqueous sodium phosphate buffer, wherein the concentration of said sodium phosphate buffer is about 5 mmol/kg to 20 mmol/kg;
   wherein the pH of said aqueous pharmaceutical composition is 7.5±0.2.

3. An aqueous pharmaceutical composition according to claim 1; comprising
   about 0.5 g/kg of the compound: 2-{4-[N-(5,6-diphenylpyrazin-2-yl)-N-isopropylamino]butyloxy}-N-(methylsulfonyl)acetamide;
   5±0.5 ww % of glycine;
   about 0.3 ww % of polysorbate 20; and
   aqueous sodium phosphate buffer, wherein the concentration of said sodium phosphate buffer is about 5 mmol/kg to 20 mmol/kg;
   wherein the pH of said aqueous pharmaceutical composition is 7.5±0.2.

4. An aqueous pharmaceutical composition according to claim 1, wherein the compound 2-{4-[N-(5,6-diphenylpyrazin-2-yl)-N-isopropylamino]butyloxy-N-(methylsulfonyl)acetamide in crystalline form is used for the preparation of said composition.

5. A method for the preparation of a lyophilized pharmaceutical composition; said method pharmaceutical comprising the steps of:
   a) preparing an aqueous pharmaceutical composition according to claim 1; and
   b) freeze-drying said aqueous pharmaceutical composition to form a cake using a method comprising the steps of:
      i) freezing the aqueous pharmaceutical composition at a first temperature for a period sufficient to transform the liquid formulation into solid state, wherein said first temperature is in the range of about −55° C. to −25° C.;
      ii) annealing the frozen composition at a second temperature; wherein said second temperature is in the range of about −20° C. to −1° C.;
      iii) subjecting the frozen composition to a vacuum at a third temperature wherein said third temperature is in the range of about −55° C. to −25° C.; and
      iv) drying the composition in said vacuum at a fourth temperature wherein said fourth temperature is in the range of about 20° C. to 40° C.

6. A lyophilized pharmaceutical composition prepared by lyophilizing an aqueous pharmaceutical composition according to claim 1.

7. A lyophilized pharmaceutical composition according to claim 6; wherein said lyophilized pharmaceutical composition is in a container.

8. A lyophilized pharmaceutical composition according to claim 6; wherein said lyophilized pharmaceutical composition has a residual water content of less than about 2 ww %.

9. A lyophilized pharmaceutical composition according to claim 6; wherein said lyophilized pharmaceutical composition is chemically stable and physically stable at room temperature and a relative humidity of about 75% or below for at least 6 months.

10. A method for the prevention or treatment of ulcer, digital ulcer, diabetic gangrene, diabetic foot ulcer, pulmonary hypertension, pulmonary arterial hypertension, Fontan disease and pulmonary hypertension associated with Fontan disease, sarcoidosis and pulmonary hypertension associated with sarcoidosis, peripheral circulatory disturbance, connective tissue disease, chronic kidney diseases including glomerulonephritis and diabetic nephropathy at any stage, diseases in which fibrosis of organs or tissues is involved, or respiratory diseases, the method comprising administering a pharmaceutically acceptable amount of a pharmaceutical composition according to claim 1 to a patient in need thereof.

11. A method for the preparation of a reconstituted pharmaceutical composition; said method comprising the step of reconstituting the lyophilized pharmaceutical composition according to claim 6 by adding at least one diluent to said lyophilized composition.

12. A reconstituted pharmaceutical composition prepared from a lyophilized pharmaceutical composition according to claim 6.

13. A reconstituted pharmaceutical composition according to claim 12; wherein said reconstituted pharmaceutical composition is in a container.

14. A reconstituted pharmaceutical composition according to claim 12; wherein said reconstituted pharmaceutical composition is reconstituted in a reconstitution time of less than about 2 minutes.

15. A reconstituted pharmaceutical composition according to claim 12; wherein said reconstituted pharmaceutical composition is reconstituted using, as diluent, water for injection or saline; wherein the total volume of said reconstituted pharmaceutical composition is between about 2 and 10 mL.

16. A reconstituted pharmaceutical composition according to claim 12; wherein said reconstituted pharmaceutical composition, or a part of said reconstituted pharmaceutical composition, is further diluted; wherein said reconstituted and further diluted pharmaceutical composition contains an amount of about 4.5 μg/mL, 9 μg/mL, 13.5 μg/mL, 18 μg/mL, 22.5 μg/mL, 27 μg/mL, 31.5 μg/mL, or 36 μg/mL of the compound 2-{4-[N-(5,6-diphenylpyrazin-2-yl)-N-isopropylamino]butyloxy}-N-(methylsulfonyl)acetamide.

17. A reconstituted and further diluted pharmaceutical composition according to claim 16; wherein said reconstituted and further diluted pharmaceutical composition has an osmolality of below about 1000 mOsmol/kg.

\* \* \* \* \*